United States Patent [19]

Shturman

[11] Patent Number: 5,331,947
[45] Date of Patent: Jul. 26, 1994

[54] INFLATABLE SHEATH FOR INTRODUCTION OF ULTRASONIC CATHETER THROUGH THE LUMEN OF A FIBER OPTIC ENDOSCOPE

[75] Inventor: Leonid Shturman, Minneapolis, Minn.

[73] Assignee: Shturman Cardiology Systems, Inc., Minnetonka, Minn.

[21] Appl. No.: 877,692

[22] Filed: May 1, 1992

[51] Int. Cl.$^5$ .............................................. A61B 1/00
[52] U.S. Cl. .................................. 126/4; 126/662.06; 604/96
[58] Field of Search ................ 128/4, 6, 662.06; 604/96

[56] References Cited

U.S. PATENT DOCUMENTS

| | | | |
|---|---|---|---|
| 4,794,931 | 1/1989 | Yock | 128/660.03 |
| 4,887,606 | 12/1989 | Yock et al. | 128/662.05 |
| 4,917,097 | 4/1990 | Proudian et al. | 128/662.06 |
| 4,951,677 | 6/1990 | Crowley et al. | 128/662.06 |
| 5,000,185 | 3/1991 | Yock | 128/662.03 |
| 5,010,886 | 4/1991 | Passafaro et al. | 128/660.03 |
| 5,024,234 | 6/1991 | Leary et al. | 128/663.01 |
| 5,025,778 | 6/1991 | Silverstein et al. | 128/4 |
| 5,029,588 | 7/1991 | Yock et al. | 128/662.06 |
| 5,054,492 | 10/1991 | Scribner et al. | 128/662.06 |
| 5,156,612 | 10/1992 | Pinchuck et al. | 604/96 X |

FOREIGN PATENT DOCUMENTS

| | | |
|---|---|---|
| 9004657 | 8/1990 | PCT Int'l Appl. . |
| 9101813 | 3/1991 | PCT Int'l Appl. . |
| 9101815 | 3/1991 | PCT Int'l Appl. . |
| 9103365 | 5/1991 | PCT Int'l Appl. . |
| 9103521 | 5/1991 | PCT Int'l Appl. . |
| 9200697 | 1/1992 | PCT Int'l Appl. ............ 128/4 |

OTHER PUBLICATIONS

Bertini, A., et al., "Rotating Probe for Trans-oesophageal Cross-sectional Echocardiography," *The Journal of Nuclear Medicine and Allied Sciences*, vol. 28, No. 2, 1984.

Bom, N., et al., "Early and Recent Intraluminal Ultrasound Devices," *International Journal of Cardiac Imaging*, 4:79-88, 1989.

Primary Examiner—Richard J. Apley
Assistant Examiner—Beverly A. Meindl
Attorney, Agent, or Firm—Gregory P. Kaihoi

[57] ABSTRACT

A inflatable sheath for ultrasonic imaging, with a fiber optic endoscope, of a bodily passageway or cavity area of interest. The inflatable sheath, having an ultrasound transducer therein, is introduced into the distal end of an endoscope. Typically the endoscope comprises an elongated shaft that has at least a pair of fiber optic bundles and an open lumen extending therethrough. Fiber optic illumination of the area just distal to the distal end of the endoscope is provided through one of the fiber optic bundles, and observation of the lit area is provided through the other bundle. The open lumen is provided for introducing an inflatable sheath, guided by a pushing shaft, into the illuminated area. Once inserted, the sheath can be inflated with a fluid sonolucent ultrasound coupling medium, and the pushing shaft can then be removed, the distal portion of the inflated sheath holding the sheath in place (with respect to the lumen of the endoscope) as the pushing shaft is removed. An ultrasonic imaging device bearing one or more ultrasonic transducer elements is then introduced through the lumen of the inflatable sheath so that the transducer elements are positioned within the sheath. The inflatable sheath is fully inflated thereafter with a fluid sonolucent ultrasound coupling medium so that the walls of the sheath engage the walls of the bodily passageway or cavity, thus permitting ultrasonic imaging of the adjacent body tissue. In certain applications, the ultrasound catheter may be preferably curved at its distal end so that the transducer elements are brought closer to or immediately adjacent to the interior surface of the inflated sheath and hence closer to the body tissue of interest. In other aspects of the disclosure, alternate apparatus and methods are provided for advancing the inflatable sheath, inflating the inflatable sheath and combining the ultrasound catheter with the pushing shaft and/or inflating catheter.

17 Claims, 17 Drawing Sheets

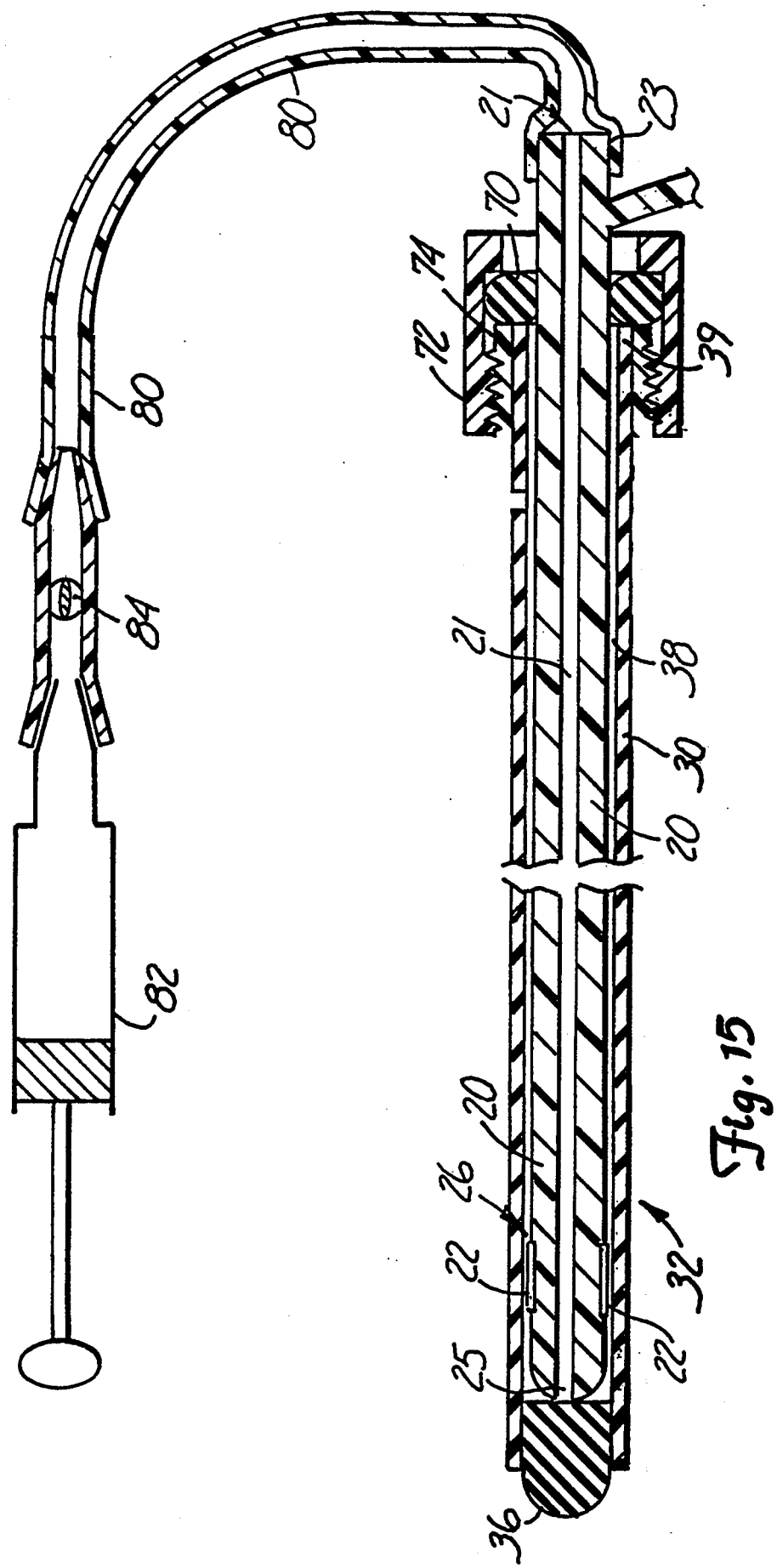

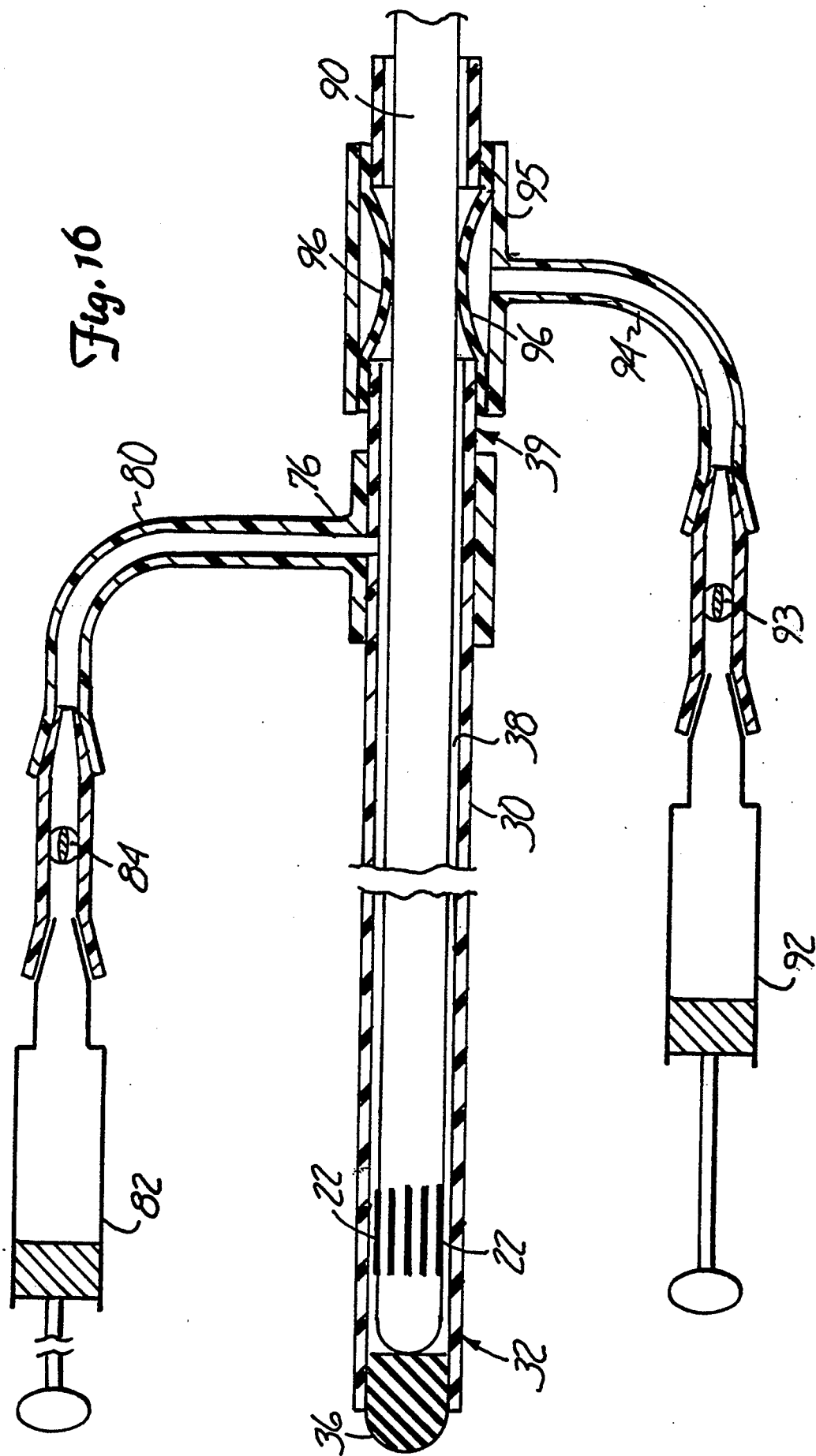

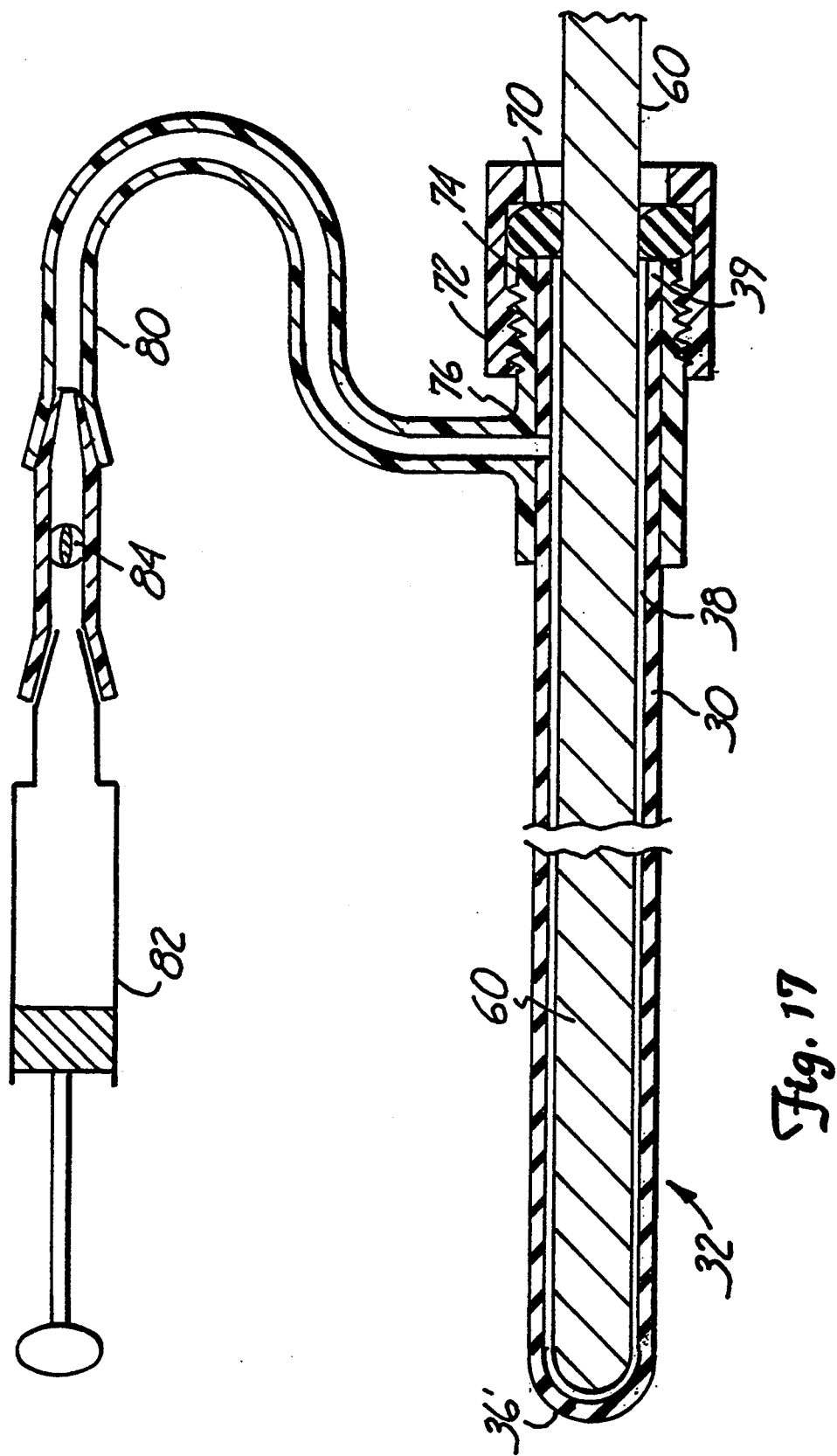

INFLATABLE SHEATH FOR INTRODUCTION OF ULTRASONIC CATHETER THROUGH THE LUMEN OF A FIBER OPTIC ENDOSCOPE

FIELD OF THE INVENTION

This invention relates to a method and apparatus for conducting transluminal ultrasound imaging, such as transbronchial ultrasound imaging, and, more particularly, to an inflatable sheath useable to introduce an ultrasound catheter through the lumen of an endoscope to a desired location in a body passageway or cavity for diagnostic ultrasound imaging of tissue adjacent thereto.

BACKGROUND OF THE INVENTION

Diagnostic ultrasound techniques and applications of transluminal ultrasound imaging to locate and diagnose pathologic conditions of body tissue or obstructions of body lumens are widely known. The book entitled *Intravascular Ultrasound—Techniques, Developments Clinical Perspectives*, edited by N. Bom and J. Roelandt (Kluwer Academic Publishers, Rotterdam Post-Graduate School of Cardiology, 1989), incorporated herein by reference, describes the equipment used in transluminal ultrasound imaging and a number of applications of such imaging.

Intraluminal ultrasound imaging is widely used in cardiology where the ultrasound transducer is mounted at the tip of a catheter introduced into the vascular system and advanced through the vessels of the heart to obtain cross-sectional ultrasound images of heart vessels at desired locations. In addition, transesophageal ultrasound imaging has been employed in cardiology to scan the heart and blood vessels adjacent to the esophagus. Most of these systems have transducers mounted on special types of tubing, although smaller transluminal devices employing distensible fluid filled bags for contact with the esophogeal wall have also been developed. See, for example, "Rotating Probe for Transoesopnageal Cross-Sectional Echocardiography" by Bertini, et al, *Nucl Med Allied Sci,* 1984; 28:115-21, incorporated herein by reference.

A wide variety of miniaturized catheter tip mounted ultrasound transducers have been developed as itemized in the first chapter of the aforementioned Bom book. Of these, the multi-element array ultrasound transducers or the rotating ultrasound element transducers or the rotating mirror ultrasound transducers provide, either through electronic switching or mechanical rotation, the ability to scan a cross section of tissue adjacent to the ultrasound transducer.

The development of transluminal ultrasound transducers to some extent coincided with the recent commercialization of percutaneous transluminal coronary angioplasty (PTCA) balloon catheters and the widespread use of endoscopes for visualizing body lumens and cavities. Endoscopes are typically designed to observe areas within a body passageway or cavity. Ordinarily, the endoscope is provided with a first fiber optic bundle to direct illumination from the proximal to the distal end of the endoscope to provide illumination of the area of interest. An additional fiber optic bundle is included to convey a visual image of the illuminated area to the physician.

Although recent advances have been made in transluminal ultrasound and particularly in transesophogeal cardiac imaging and in coronary ultrasound imaging, a number of problems remain in providing a convenient, practical way to perform transbronchial ultrasonography and in particular in combining transbronchial ultrasonography with bronchoscopy.

The bronchial system is filled with air, and thus in order to perform transbronchial ultrasonography it is necessary to fill the space between the ultrasound transducer and the tissue of interest with an ultrasound coupling medium, preferably a fluid sonolucent coupling medium.

SUMMARY OF THE INVENTION

The invention provides an apparatus and method for introducing and accurately positioning an ultrasound transducer element distally to an endoscope in order to obtain a transbronchial ultrasonic image of tissues underlying the surface area visualized through the endoscope.

The invention provides an inflatable, distensible sheath adapted to be introduced through an open lumen of an endoscope so that the distal portion of the sheath can be positioned distally of the distal end of the endoscope, adjacent to the tissue of interest which may be viewed through the endoscope. Inflation means is provided for selectively inflating the inflatable sheath with a sonolucent fluid coupling medium. When inflated, the walls of the distal portion of the sheath contact the body tissue of interest, and the walls of the remaining portion of the sheath contact the inner walls of the open lumen of the endoscope. An elongated ultrasound catheter is adapted to be disposed within the inflatable sheath when the sheath is inflated, the ultrasound catheter having an ultrasound transducer mounted at its distal tip for introduction into the distal distended portion of the inflatable sheath.

A typical endoscope usable with the inflatable sheath includes at least a pair of fiber optic bundles, one for illumination of the area of interest and the other for conducting a visual image of the area of interest to the physician. It also typically includes an open lumen for use in performing suction, advancing biopsy forceps, and the like.

In use, the endoscope is introduced into the bodily passageway or cavity of interest while visualizing the tissue adjacent the distal end thereof until a desired position is reached for ultrasound imaging. The deflated sheath is then introduced through the use of a pushing shaft disposed therein until a portion of the sheath is located distally to the distal end of the endoscope. At this point, the sheath is inflated with the ultrasonically transparent fluid coupling medium, and the pushing shaft is withdrawn. While the sheath remains inflated, the elongated ultrasound catheter is introduced in place of the pushing shaft. The fluid ultrasound coupling medium extending through the lumen of the inflatable sheath expands the sheath so that its inner diameter is larger than the outer diameter of the ultrasound catheter, thus allowing the ultrasound catheter to move longitudinally with respect to the sheath. The fluid ultrasound coupling medium also lubricates and eases the introduction of the ultrasound catheter into the inflatable sheath, and, if the medium is radio-opaque, it will facilitate fluoroscopic imaging of the position and degree of inflation of the distal portion of the sheath. After the ultrasound catheter is positioned within the sheath, the sheath usually is further expanded so that its distal end portion (i.e., the portion extending distally of the endoscope lumen) abuts the tissue of interest for ultrasound imaging.

In alternate preferred embodiments, the shaft of the ultrasound catheter may be sufficiently stiff so that it can function as the pushing shaft or introducer for the inflatable sheath. The fluid coupling medium may be introduced through a hollow pushing shaft or introducer which may or may not also constitute the ultrasound catheter. The inflatable sheath may also be constructed in accordance with alternate embodiments.

In any of these embodiments, in some cases it is desirable to provide the ultrasound catheter with a distal bend or offset section adjacent to or including the ultrasound transducer element or elements so that, in use, the transducer elements may be positioned closer to or against the inner wall of the expanded sheath so as to be positioned closer to tissue of interest.

In accordance with a preferred embodiment of the present invention, it is especially adapted for use in a transbronchial ultrasound imaging.

BRIEF DESCRIPTION OF THE DRAWINGS

These and other objects, advantages and features of the present invention will be apparent to those of skill in the art from the following detailed description of the preferred embodiments and the accompanying drawings in which the same or equivalent elements are designated by the same or like numerals, and in which:

FIG. 15 is a partial cross-section view of a further embodiment of the ultrasound catheter and/or pushing shaft and apparatus for inflating the inflatable sheath with fluid advanced through the lumen of the combined ultrasound catheter/pushing shaft.

FIG. 16 is a partial cross-section view of an embodiment of the invention similar to FIG. 9 illustrating a structure for sealing the proximal end of the inflatable sheath.

FIG. 17 is a partial cross-section view of a modified embodiment of the invention similar to FIG. 2, showing an alternate integral distal end of the inflatable sheath. It will be understood that the drawings are not to scale and are schematic representations of components known in the art.

DESCRIPTION OF THE PREFERRED EMBODIMENTS

Figure 1:
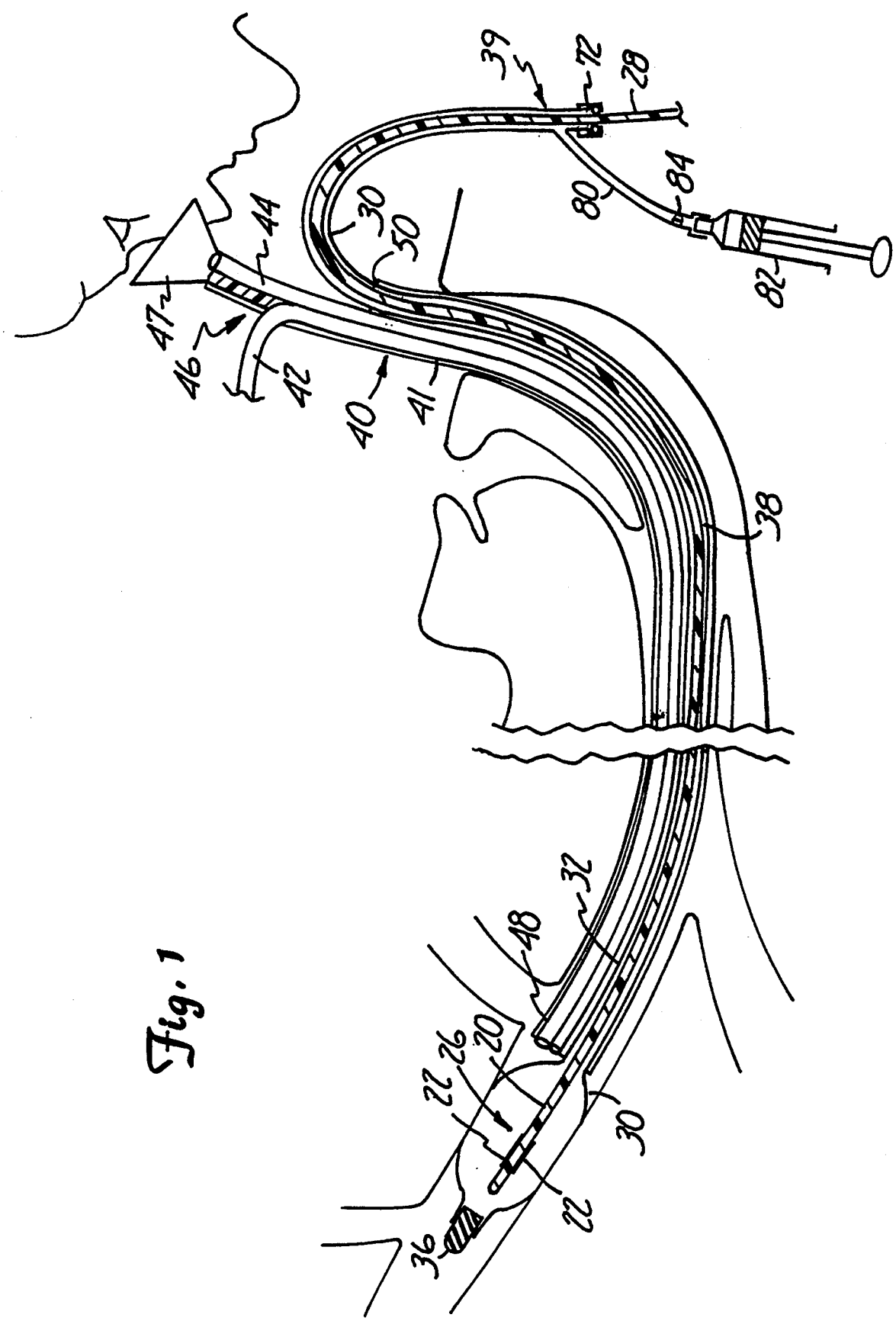
FIG. 1 is a schematic perspective view in partial cross-section of an ultrasound catheter advanced inside the inflatable sheath of the present invention through the open lumen of an endoscope into the bronchial system of a patient.

FIG. 1 illustrates in partial cross section the ultrasound catheter 20 positioned within the inflatable sheath 30, extending through a fiber optic endoscope 40, and advanced to a desired location in a patient's bronchial passageway. For example, the distal most components are illustrated as residing in the truncus intermedius (a major bronchus) of the right lung in order to conduct an ultrasound examination of tissues surrounding the bronchus including the wall of the bronchus itself. The assembled ultrasound catheter 20 and sheath 30 encased within a lumen of the fiber optic endoscope 40 have been advanced through the patient's nostril, nasopharynx, larynx, and the trachea to reach the illustrated position in a manner well known in the art. As illustrated in FIG. 1, a physician is viewing the expanded inflatable sheath which is illuminated by an external light source (not shown), by way of a first, illuminating fiber optic bundle 42 through an eyepiece 47 connected to a second, imaging fiber optic bundle 44 extending from the proximal end 46 of the endoscope 40 to its distal end 48.

The inflatable sheath 30 comprises a stretchable, expandable tube extending through an open lumen 50 in the endoscope 40 and inflated with a fluid coupling medium so that in its distal portion 32 the walls of the expanded inflatable sheath 30 contact the walls of the truncus intermedius. The ultrasound coupling provided by the sonolucent fluid medium inside the inflated distal portion 32 of the inflatable sheath 30 allows the ultrasound transducer element 22 to scan the tissue adjacent to the expanded sheath. The electrical signals to and from the ultrasound transducer are conducted through conducters to and from conventional ultrasound generating, processing, and recording equipment (not shown but described in the above incorporated publications) connected to the proximal end 28 of the ultrasound catheter 20.

The inflatable sheath 30 is terminated at its distal end with a plug 36. This plug 36 may be made of plastic material, silicone, or other suitable materials. FIG. 17 illustrates an alternative embodiment in which the inflatable sheath 30 is manufactured with an integral molded distal end 36', thus eliminating the plug 36 shown in FIG. 2.

Figure 2:
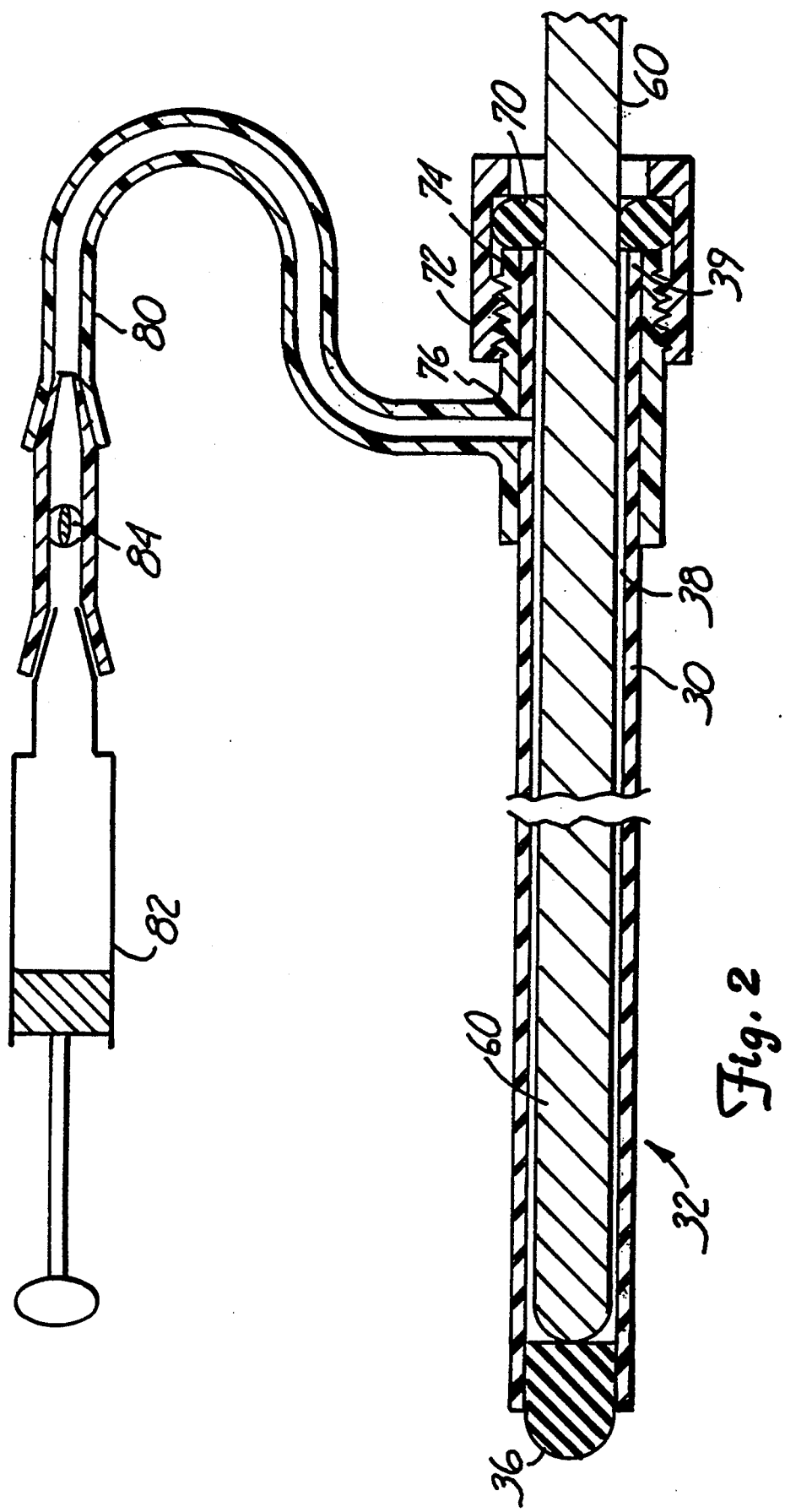
FIG. 2 is a partial cross-section view of an assembled pushing shaft and inflatable sheath and apparatus for filling the sheath with fluid coupling medium.

A pushing shaft 60 is employed, as described below, to facilitate the advancement of the inflatable sheath 30 through an open lumen in the endoscope 40. FIG. 2 illustrates how the pushing shaft 60 (and subsequently the ultrasound catheter 20) is introduced into the lumen 38 of the inflatable sheath 30 through a sealable valve 70 which is locked in a valve housing 72 that is screwed tightly on the distal end 74 of a fitting 76 that surrounds the proximal end 39 of the inflatable sheath 30 in a manner well known in the art, e.g., relating to vascular introducers and balloon catheters for coronary and peripheral angioplasty.

In order to inflate the inflatable sheath 30, a sonolucent fluid coupling medium is expelled from a syringe 82 through stopcock 84 and tubing 80 into the space 38 between the pushing shaft 60 and the expandable sheath 30 to expand the sheath 30 including its distal end portion 32 which is not confined in the open lumen of the endoscope 40.

Figure 3:
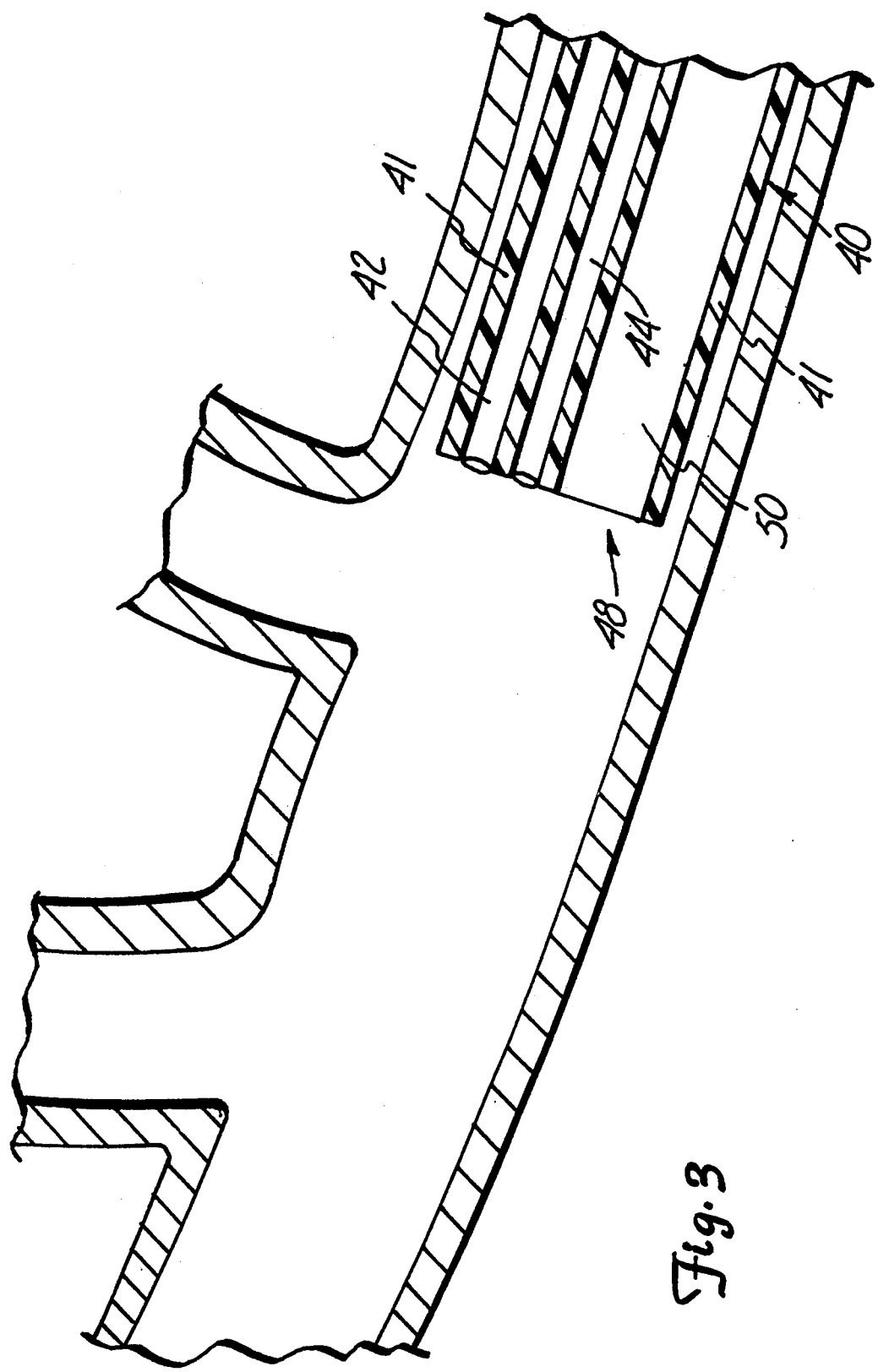
FIGS. 3–8 are illustrations of the steps of the method of introducing and using the assembly depicted in FIG. 1.

Turning now to FIGS. 3 to 8, the steps of practicing the present invention in a first embodiment thereof employing the apparatus depicted in FIGS. 1 and 2 are illustrated. FIG. 3 depicts in partial cross-section the distal end 48 of the endoscope 40 at the end of the right main bronchus immediately proximally to the junction of the upper lobe bronchus with the truncus intermedius. The fiber optic endoscope 40 comprises a tube 41 containing a pair of fiber optic bundles and an open lumen 50 extending therethrough. The open lumen 50 accommodates and receives the inflatable sheath 30 and the pushing shaft 60 and/or the ultrasound catheter 20 therein as depicted in FIGS. 1 and 2. As descibed above, tube 41 of the endoscope 40 encloses the first light transmitting fiber optic bundle 42 and the second imaging fiber optic bundle 44. The construction of such endoscopes for direct endoscopic visualization and passage of operating instruments such as biopsy forceps through the open lumen of the endoscope is well known in the art. Of course, to the extent that visual imaging systems other than fiber-optic based systems (e.g., CCD or other electronic based systems) are utilized in an endoscope, the present invention could also be used with such an endoscope.

FIG. 3 illustrates the initial positioning of the distal end 48 of the endoscope 40 immediately proximally to a site that has been selected for transbronchial imaging and identified by the physician observing through the endoscope. In the same fashion, the invention can be utilized with an endoscope guided through the gastrointestinal tract, the urinary tract, or similar bodily passageway or cavity.

Figure 4:
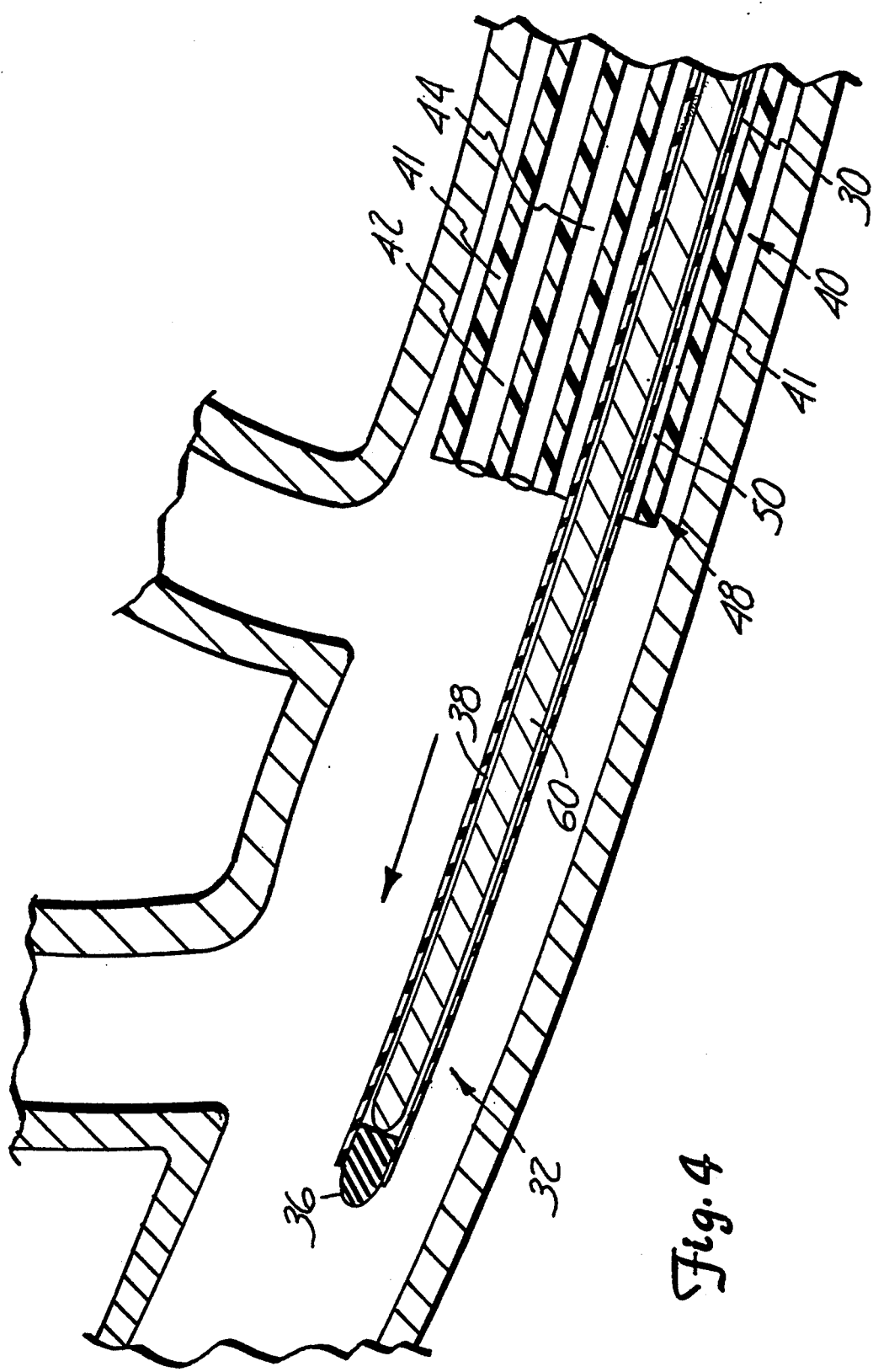

Turning now to FIG. 4, it illustrates the longitudinal advancement of the distal portion 32 of the inflatable sheath 30 through the lumen 50 of the endoscope 40 to an area of the bronchus, the cross section of which is to be imaged. The advancement is accomplished through the use of the pushing shaft 60 disposed in the lumen 38 of the inflatable sheath 30. In practice, the physician observes, through the endoscope 40, the distal end portion 32 of the sheath 30 as he advances it out of the distal end 48 of the endoscope 40.

Figure 5:
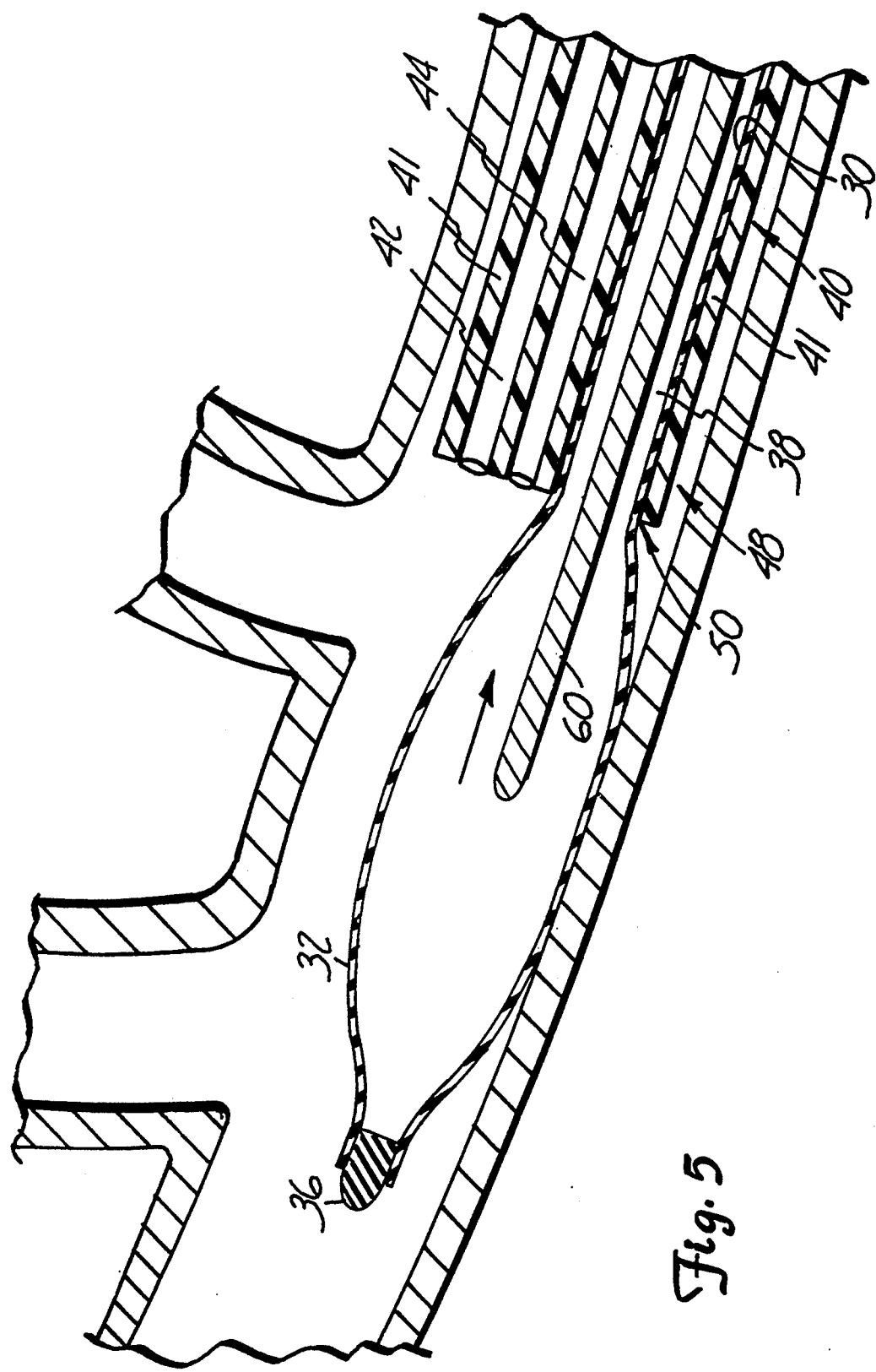
Figure 6:
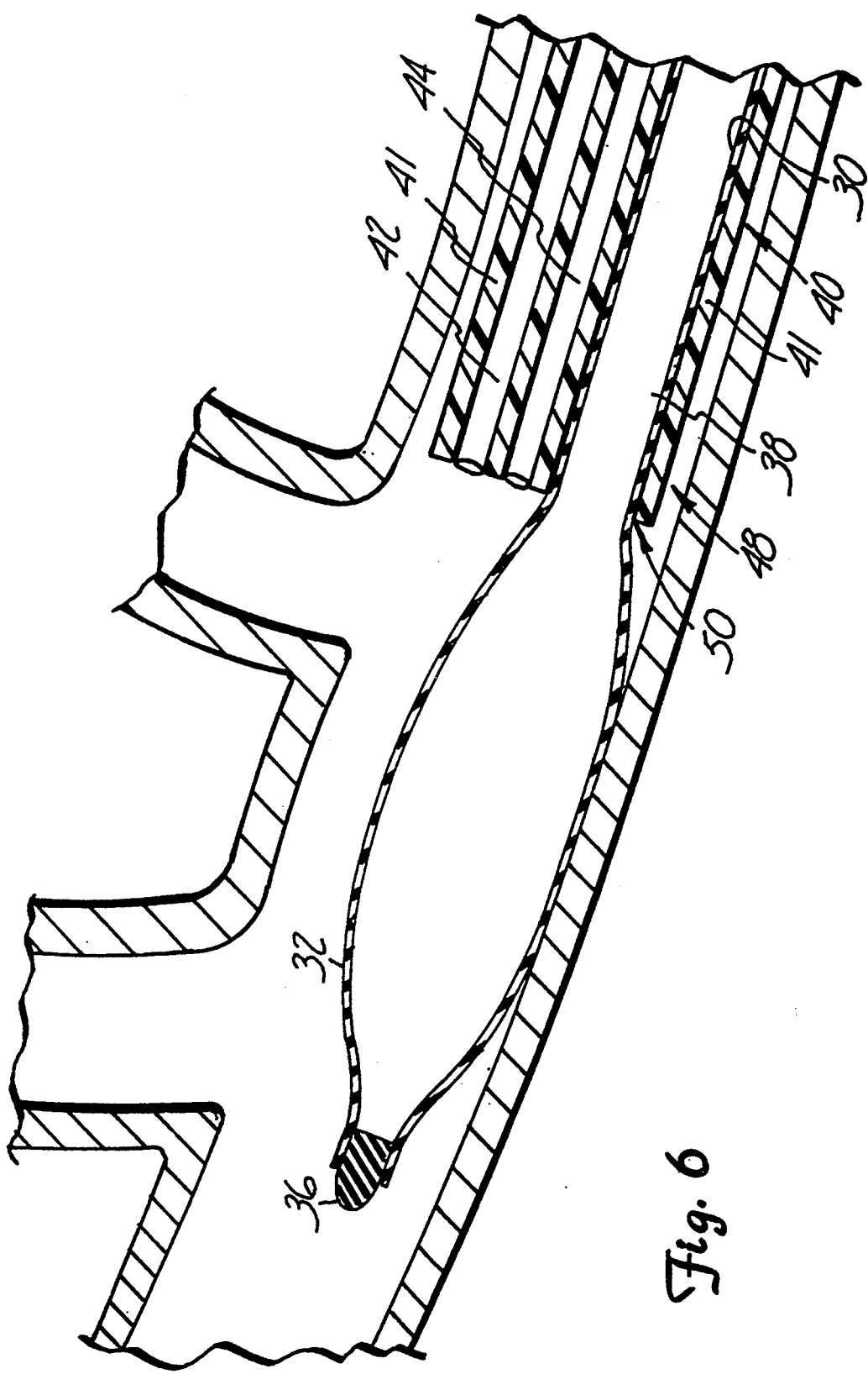

FIGS. 5 and 6 illustrate the partial expansion of the distal segment 32 of the sheath 30 with sonolucent fluid coupling medium in the manner described with respect to FIG. 1 and the withdrawal of the pushing shaft 60 through the expanded lumen 38 of the inflatable sheath 30. Once the pushing shaft 60 is withdrawn through the sealable valve 70, the distal end segment 32 of the inflatable sheath 30 remains at least partially inflated and anchors the distal portion 32 of the inflatable sheath 30 distally to the distal end 48 of the endoscope 40.

Figure 7:
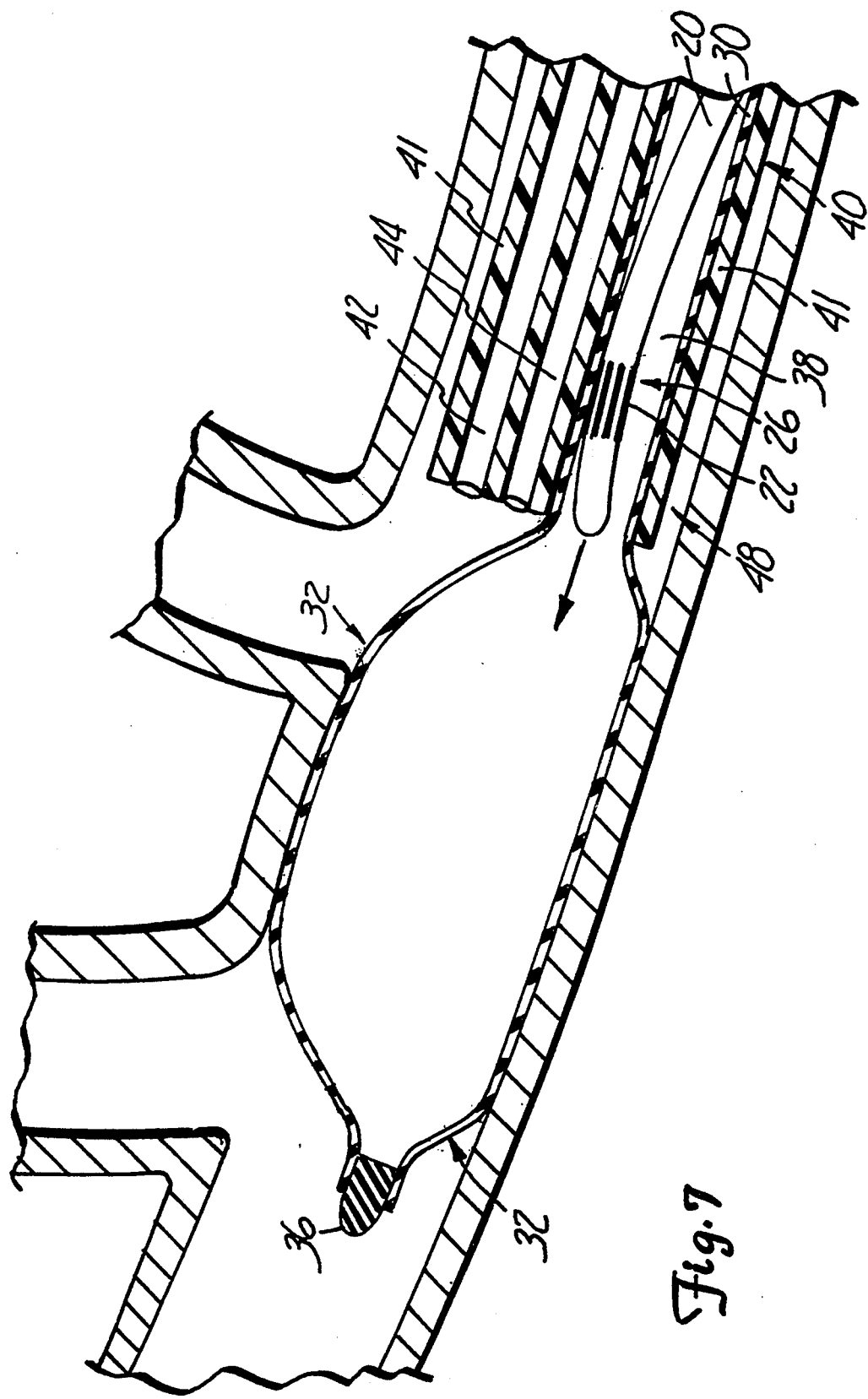

In FIG. 7, the distal end segment 26 of the ultrasound catheter 20 including the array of transducer elements 22 is depicted as it is advanced through the expanded lumen 38 of the inflatable sheath 30 toward the distal distended portion 32 of the sheath. In this illustration, a distal segment 26 of the ultrasound catheter 20 is curved in order to facilitate positioninq of the transducers close to the wall of the expanded distal portion 32 of the sheath 30 as depicted in FIG. 8.

Figure 8:
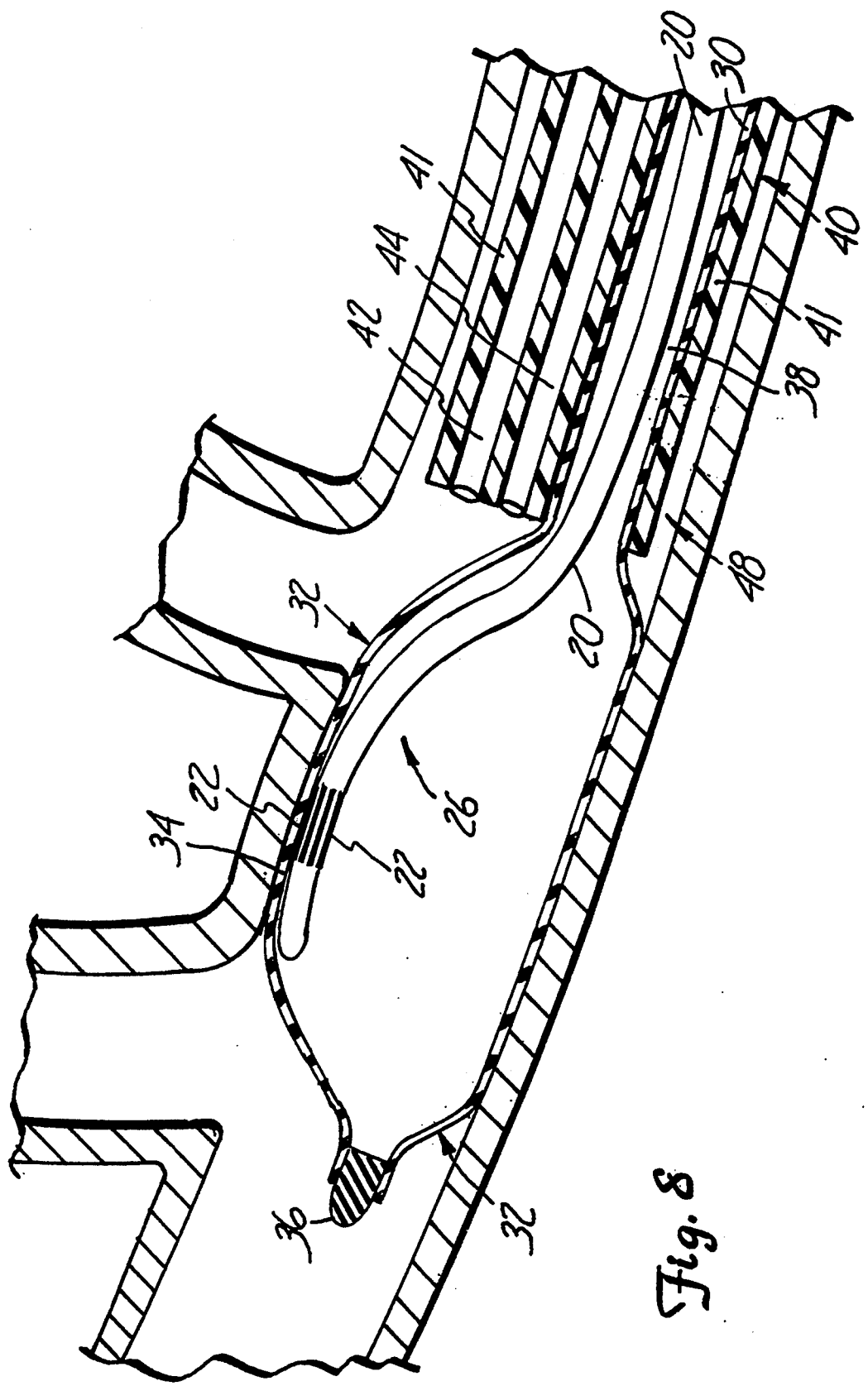

FIG. 8 illustrates that when the curved distal segment 26 of the ultrasound catheter 20 enters the expanded distal portion 32 of the inflatable sheath 30 and is no longer restricted in its lateral movement by the open lumen 50 of the endoscope 40, it is freed to regain its original preformed shape. Thus, the curved distal segment 26 positions the transducer elements 22 closer to or adjacent to the wall 34 of the distal portion 32 of the inflatable sheath 30. This position of the transducer elements 22 facilitates imaging of the wall of the truncus intermedius and of the tissue immediately adjacent to the wall of the bronchus. As each tissue segment is scanned, the distal end of the ultrasound catheter 20 may be rotated to move the ultrasound transducer elements 22 radially around the wall 34 of the inflated distal portion 32 of the inflatable sheath 30. This movement and confirmation of the desired scanning position may be observed by the physician through the fiber optic bundle 44 under illumination through fiber optic bundle 42 if the inflatable sheath 30 is made from a suitable transparent material. It will be understood that the distal segment 26 of the ultrasound catheter 20 may be curved or may be left straight, as desired.

If the inflatable sheath 30 is filled with a fluid which is both sonolucent and radio-opaque, then the position, amount of inflation, etc. of the distal end portion 32 of the inflatable sheath 30 can be viewed flouroscopically as well.

Figure 9:
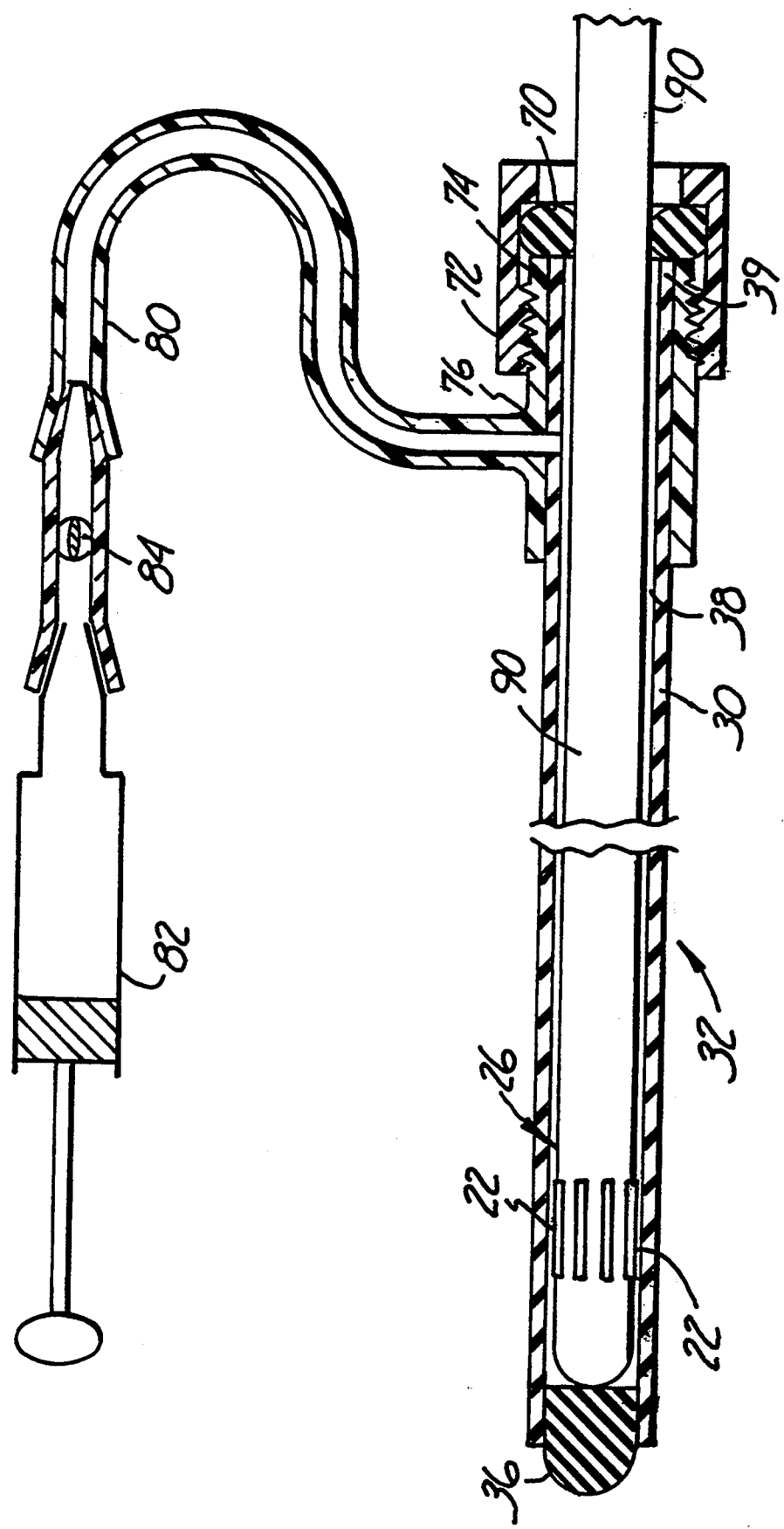
FIG. 9 is a partial cross-section view of a second embodiment of the present invention where the pushing shaft and ultrasound catheter are combined in a single device.

FIGS. 9 to 13 illustrate a second embodiment of the present invention wherein the pushing shaft 60 and the ultrasound catheter 20 are combined into a single unit thereby eliminating the separate pushing shaft and the steps of advancing and withdrawing it before advancing the ultrasound catheter. In FIG. 9, the combined pushing shaft and ultrasound catheter 90 is shown in the same position as the pushing shaft 60 depicted in FIG. 2, that is, fully advanced within the lumen 38 prior to inflation of the inflatable sheath 30.

Figure 10:
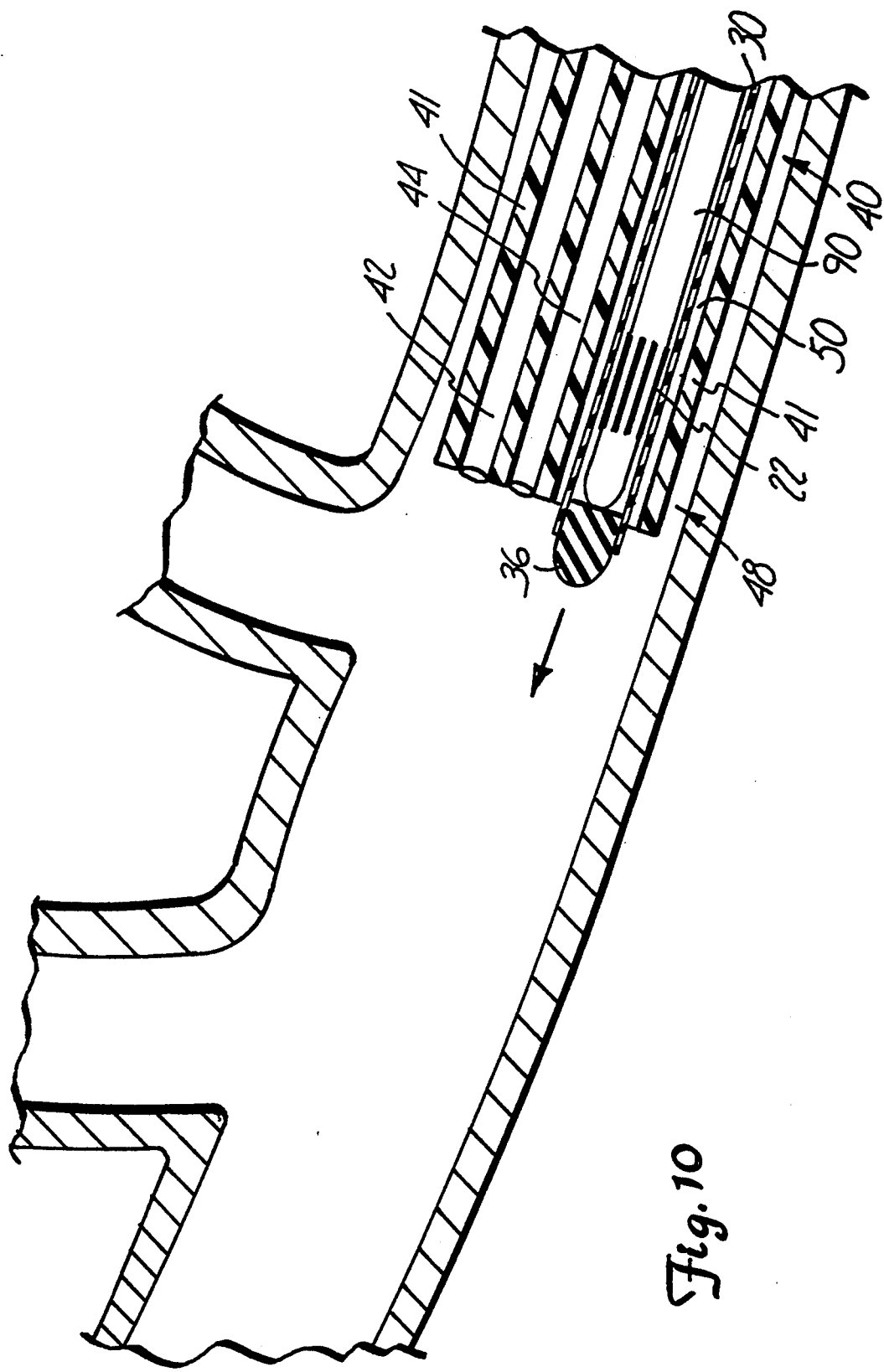
FIGS. 10–13 illustrate in partial cross-section views the method of employing the combined pushing shaft and ultrasound catheter of FIG. 9 in the procedure illustrated in FIG. 1.
Figure 11:
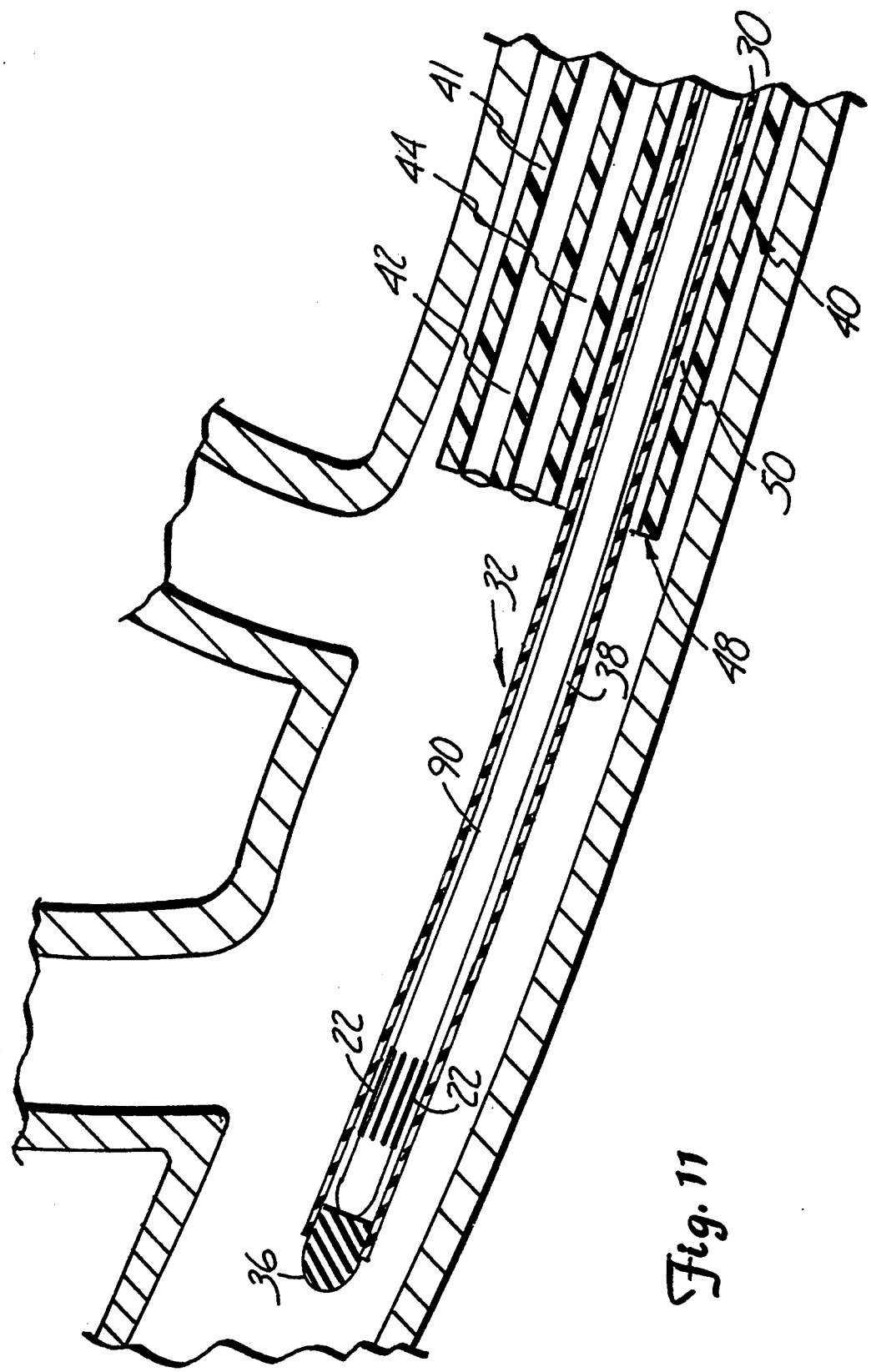
Figure 12:
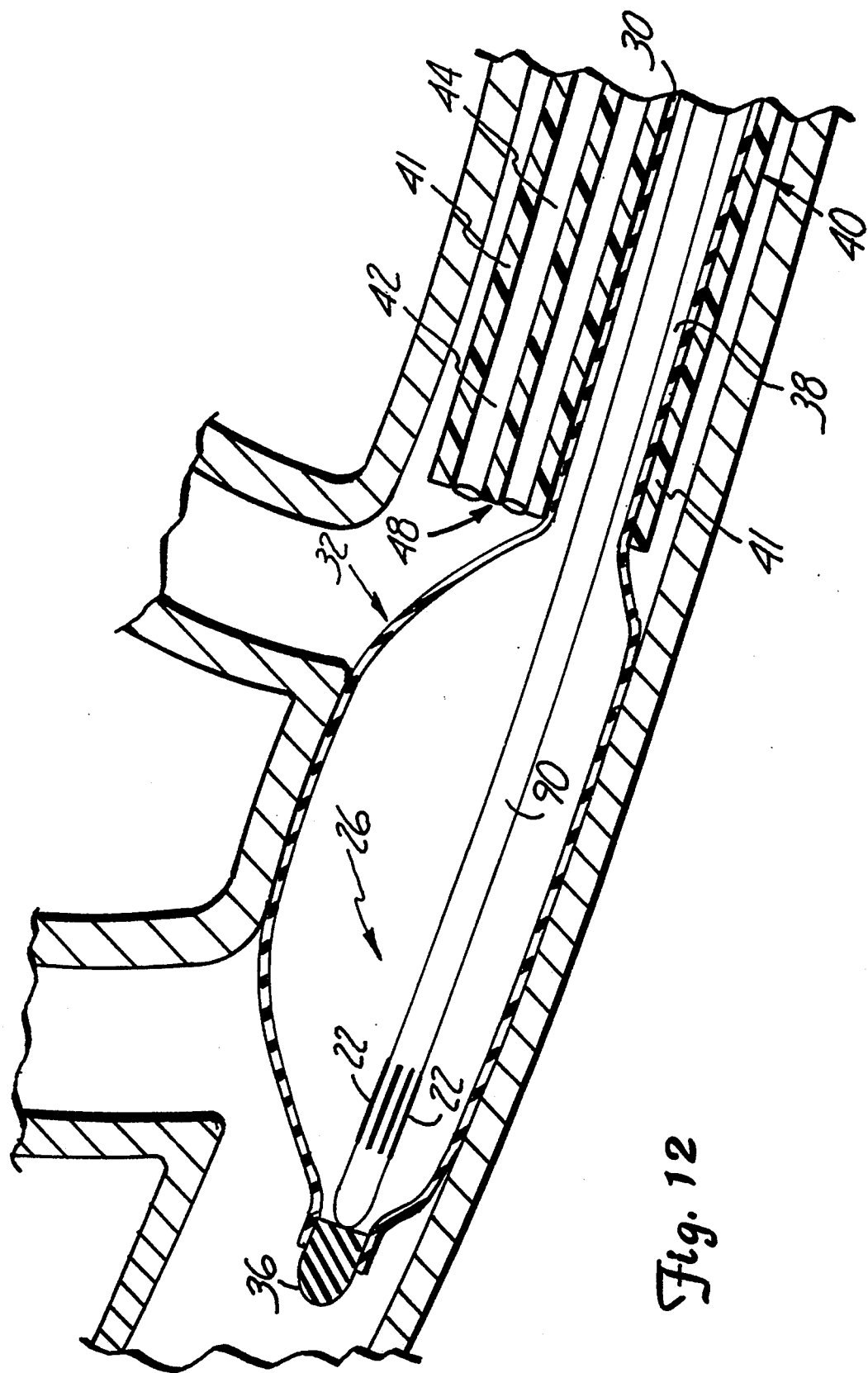
Figure 13:
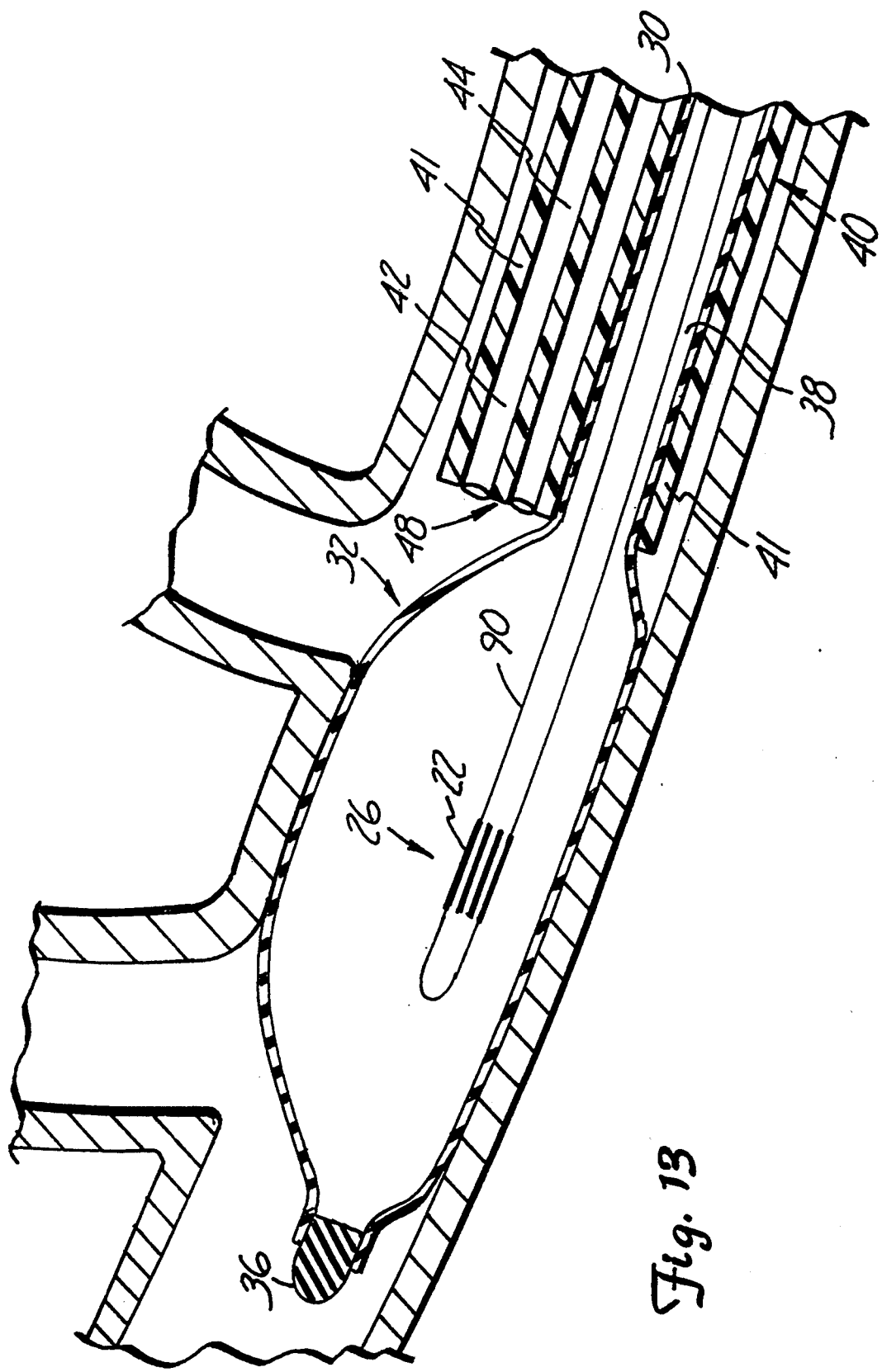

In FIGS. 10 and 11, the combined ultrasound catheter 90 is advanced into the desired position past the distal end 48 of the fiber optic endoscope 40. In FIG. 12, the sheath 30 and its distal portion 32 are expanded in the manner described above and, in FIG. 13, the straight distal segment 26 of the combined ultrasound catheter 90 is manipulated longitudinally within the confines of the expanded distal portion 32 of the sheath 30 to position the array of transducer elements 22 in a desired position with respect to the tissue to be scanned. Thus, in this embodiment, the apparatus and method are simplified by the combination of the pushing shaft with the ultrasound catheter.

Figure 14:
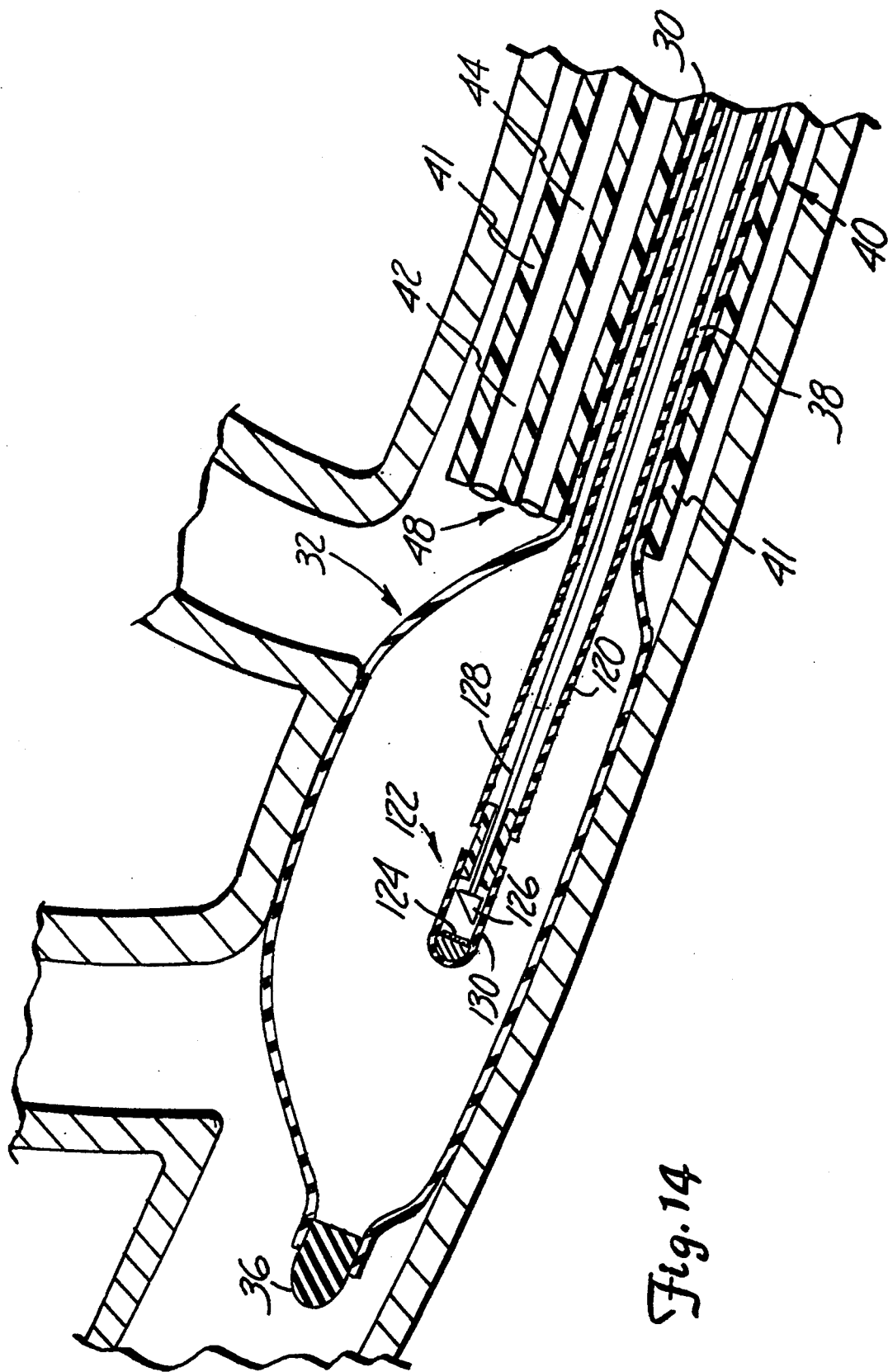
FIG. 14 is a partial cross-section view illustrating the use of an alternate, rotating element, ultrasound catheter in the apparatus and procedure depicted in FIG. 1.

Turning now to FIG. 14, a further embodiment of the present invention is illustrated wherein a rotating mirror ultrasound transducer 122 is substituted for the array of ultrasound elements 22 and associated electronic switching circuitry. The ultrasound transducer array 22 previously described may consist of many small acoustic elements which are positioned cylindrically around the catheter tip. The number of elements may be any practical binary number such as 16, 32, 64 or 128. Subject to size considerations, the tip may contain integrated circuitry for reducing the number of conductors extending down the length of the body of the device 20. The details of such a multi-element ultrasound transducer array and the associated switching and signal processing circuits are disclosed in the aforementioned incorporated publication.

In reference to FIG. 14, the rotating mirror transducer element 122 comprises an echo transducer 124 coupled electrically by conductors (not shown) extending down the length of the transducer catheter 120 and a rotatable 90° acoustic reflecting mirror 126 which is cause to rotate by a shaft 128 coupled at the proximal end to a small motor (not shown). These components are mounted in an acoustically transparent dome 130 so that as the mirror 126 rotates, it deflects the accoustic beam radially to the axis of the ultrasound catheter 120.

The non-moving transducer 124 avoids the necessity of rotating its conductors down the length of the catheter 120. Further details of the rotating mirror transducer are described in the above incorporated publications. Other types of ultrasound catheters may also be utilized, as desired.

FIG. 15 shows an alternative manner of conducting the sonolucent fluid coupling medium into the lumen 38 of the inflatable sheath 30 through a lumen 21 extending the length of the ultrasound catheter 20. In this embodiment, the tube 80 is coupled to a fitting 23 on the proximal end of the ultrasound catheter 20 communicating with the lumen 21, which has an exit port 25 at the distal end of the ultrasound catheter 20. Thus, as the fluid is expelled from the syringe 82, it is directed through the lumen 21 to expand the sheath 30 and its distal portion 32 after the sheath 30 is introduced into the position depicted, for example, in FIGS. 4 and 5.

It will be understood that the embodiment of FIG. 15 may also be incorporated into the pushing shaft or the combined pushing shaft and ultrasound catheter 90 depicted in FIG. 9. It should also be understood that the exit port or ports 25 may extend radially through the side wall of the catheters 20 or 90 at a position proximal to or distal to the transducer elements 22 or the alternate element 122. The lumen 21 may extend for substantially the entire length of the catheters 20 or 90, or the exit port(s) 25 may be located more proximally to discharge fluid into the lumen 38 at any location distal to the sealable valve 72. It will also be understood that the lumen 21 may be oriented off-center in order to accommodate specific transducer element configurations and requirements.

FIG. 16 depicts an alternate means for sealing the proximal end 39 of the inflatable sheath 30 around the combined pushing shaft and ultrasound catheter 90 (this configuration could also be used with the ultrasound catheter 20). In this embodiment, a fitting 95 is secured to the proximal end of the inflatable sheath 30. The fitting 95 is preferably generally cylindrical, and carries an inflatable, inwardly distensible balloon 96. The balloon 96 in turn is in fluid communication through tube 94 and stopcock 93 with an inflation syringe 92 for selectively inflating the balloon 96. Although the invention has been specifically disclosed in reference to various preferred embodiments thereof and in relation to a bronchoscopy procedure employed in pulmonary medicine, it will be understood that the invention and its embodiments have application to other medical uses within the scope of the invention as disclosed and claimed.

What is claimed is:

1. An ultrasound imaging apparatus for use with an endoscope for imaging a bodily passageway or cavity area of interest, the endoscope being of the type having proximal and distal ends and an open lumen therein, the ultrasound imaging apparatus comprising an elongated ultrasound transducer-bearing catheter or guide wire adapted to be disposed within the open lumen of the endoscope, the ultrasound catheter or guide wire having proximal and distal ends, wherein the improvement comprises:

an inflatable, substantially readily distensible, distally closed sheath being of a sufficient length to cover substantially the entire length of the ultrasound catheter or guide wire, the sheath being adapted to be advanced through the open lumen of the endoscope so that a distal end portion of the sheath may be positioned distally of the endoscope;

the ultrasound catheter or guide wire being adapted to be disposed within the sheath so that the ultrasound transducer is disposed in the sheath's distal end portion positioned distally of the endoscope; and means for selectively inflating the sheath to expand it against the open lumen of the endoscope and to form an expanded, substantially readily distensible balloon distally of the endoscope to engage a wall of the bodily passageway or cavity area of interest; whereby an ultrasound image of the area of interest may be obtained through the sheath in its inflated, distended condition.

2. The apparatus of claim 1 wherein the ultrasound catheter is movable longitudinally along the inflatable sheath when the sheath is inflated.

3. The apparatus of claim 1 wherein the inflatable sheath comprises a distensible sheath adapted to be disposed in the lumen of the endoscope, the portion of the sheath ext ending beyond the distal end of the endoscope being distensible to engage a wall of the bodily passageway or cavity area of interest.

4. The apparatus of claim 1 wherein the elongated ultrasound catheter includes a lumen through which sheath inflation sonolucent fluid ultrasound coupling medium can be injected.

5. The apparatus of claim 1 wherein the inflatable sheath comprises an elongated distensible tube having a proximal end, the apparatus further including sealable fitting means for sealing the proximal end of the inflatable sheath to the ultrasound catheter and for permitting the ultrasound catheter to be advanced into or withdrawn from the inflatable sheath.

6. The apparatus of claim 5 wherein the sealable fitting means comprises a generally cylindrical fitting and an inflatable, inwardly distensible balloon carried by the fitting.

7. The apparatus of claim 1 further comprising pushing shaft means adapted to be positioned within the inflatable sheath for introducing and passing the inflatable sheath through the open lumen of the endoscope and for advancing the distal end thereof into the area of interest.

8. The apparatus of claim 1 wherein the transducer-bearing catheter includes a lumen extending longitudinally therethrough; and wherein said means for selectively inflating the inflatable sheath is coupled to the proximal end of the ultrasound catheter for inflating the inflatable sheath through the lumen of the ultrasound catheter.

9. The apparatus of claim 8 wherein the inflatable sheath comprises an elongated distensible tube having a distal end sealed with a plug and a proximal end, and further including sealable fitting means for sealing the proximal end of the sheath to the ultrasound catheter and for permitting the ultrasound catheter to be advanced into or withdrawn from the inflatable sheath.

10. The apparatus of claim 1 further including an elongated pushing shaft means adapted to be disposed within the inflatable sheath for providing support to the inflatable sheath as it is advanced through the open lumen of the endoscope, the pushing shaft including a lumen extending longitudinally therethrough; and wherein said means for selectively inflating the inflatable sheath is coupled to the proximal end of the pushing shaft for inflating the inflatable sheath through the lumen of the pushing shaft.

11. An ultrasound imaging apparatus for use with an endoscope for imaging a bodily passageway or cavity area of interest, the endoscope being of the type having proximal and distal ends and an open lumen therein, the ultrasound imaging apparatus comprising an elongated ultrasound transducer-bearing catheter adapted to be disposed within the open lumen of the endoscope, the ultrasound catheter having proximal and distal ends, wherein the improvement comprises:

an inflatable, substantially readily distensible sheath comprising an elongated distensible tube having a proximal end and having a distal end sealed with a plug, the tube being of a sufficient length to cover substantially the entire length of the ultrasound catheter, the sheath being adapted to be advanced through the open lumen of the endoscope so that a distal end portion of the sheath may be positioned distally of the endoscope;

the ultrasound catheter being adapted to be disposed within the sheath and movable longitudinally along the inflatable sheath when the sheath is inflated so that the ultrasound transducer may be disposed in the sheath's distal end portion positioned distally of the endoscope, the ultrasound catheter including a lumen through which sheath inflation sonolucent fluid ultrasound coupling medium can be injected;

scalable fitting means for scaling the proximal end of the sheath to the ultrasound catheter and for permitting the ultrasound catheter to be advanced into or withdrawn from the inflatable sheath; and means for selectively inflating the sheath to expand it against the open lumen of the endoscope and to form an expanded, substantially readily distensible balloon distally of the endoscope to engage a wall of the bodily passageway or cavity area of interest;

whereby an ultrasound image of the area of interest may be obtained through the sheath in its inflated, distended condition.

12. The combination ultrasound and fiber optic endoscope of claim 10 wherein the ultrasound transducer-bearing catheter further comprises a lumen extending from the proximal end thereof and into communication with the interior of the sheath; and wherein said means for selectively inflating the inflatable sheath is coupled to the proximal end of the ultrasound catheter for inflating the inflatable sheath through the lumen thereof.

13. A combination ultrasound and fiber optic endoscope for imaging a bodily passageway or cavity area of interest, comprising:

an elongated, flexible fiber optic endoscope having proximal and distal ends and an open lumen therein, such open lumen having an inner wall;

an elongated flexible optical fiber extending through the endoscope from the proximal to the distal end thereof and illumination meant associated therewith for providing light through the fiber to visually illuminate the area of interest, and a separate optical fiber extending through the endoscope from the distal to the proximal end thereof and imaging means associated therewith for transmitting a visual image from the area of interest to the proximal end of the endoscope;

an inflatable, substantially readily distensible, distally closed sheath adapted to be advanced through the open lumen of the endoscope so that a distal end portion of the sheath may be positioned distally of the endoscope's open lumen;

means for selectively inflating the sheath to expand the portion of the sheath disposed in the endoscope's open lumen against the lumen's inner wall, and to form an expanded, substantially readily distensible balloon distally of the endoscope to engage a wall of the bodily passageway or cavity area of interest;

an elongated ultrasound transducer-bearing catheter or guide wire adapted to be disposed within the inflatable sheath within the open lumen of the endoscope, the ultrasound catheter or guide wire having proximal and distal ends and ultrasound transducer means carried near its distal end for providing an ultrasound image of the area of interest;

the sheath being of a sufficient length to cover substantially the entire length of the ultrasound catheter or guide wire, and the ultrasound catheter or guide wire being adapted to be disposed within the sheath and movable longitudinally with respect thereto when the sheath is inflated so that the ultrasound transducer may be selectively disposed in the sheath's distal end portion positioned distally of the endoscope;

whereby an ultrasound image of the area of interest may be obtained through the sheath in its inflated, distended condition.

14. A method of transluminal ultrasound imaging of body tissue of interest adjacent to a bodily passageway or cavity employing an ultrasound catheter or guide wire having one or more ultrasound transducer elements on the distal portion thereof and an endoscope which has proximal and distal ends and an open lumen therethrough, comprising the steps of:

introducing the endoscope into a desired position in a body passageway or cavity area of interest;

introducing an elongated, inflatable, substantially readily distensible, distally closed sheath having proximal and distal ends through the open lumen of the endoscope until a distal end portion thereof is positioned distally of the endoscope and adjacent the tissue of interest;

inflating the elongated inflatable sheath with a fluid sonolucent ultrasound coupling medium so that the portion of the sheath disposed in the endoscope lumen is distended against the lumen inner wall and the portion of the sheath extending distally of the endoscope is distended to substantially fill the bodily passageway or cavity area adjacent the tissue of interest;

inserting the ultrasound catheter or guide wire into the sheath so that substantially the entire length of the ultrasound catheter or guide wire is disposed within the inflatable sheath with the ultrasound transducer element(s) positioned near the tissue of interest; and ultrasonically imaging the tissue of interest through the expanded sheath filled with fluid sonolucent ultrasound coupling medium.

15. The method of claim 14 further comprising the steps of:

inserting a pushing shaft into the distensible inflatable sheath;

introducing and advancing the inflatable sheath and pushing shaft through the open lumen of the endoscope until the distensible sheath is positioned distally of the endoscope; and withdrawing the pushing shaft after placement of the distensible sheath in the area of interest of inflation of the sheath.

16. The method of claim 15 further comprising the steps of:

partially inflating the sheath with the fluid sonolucent ultrasound coupling medium while the pushing shaft is in place; and fully inflating the sheath with the fluid sonolucent ultrasound coupling medium after withdrawal of the pushing shaft and advancement of the ultrasound transducer-bearing catheter into the inflatable sheath.

17. The method of claim 14 wherein the inflating step includes inflating the inflatable sheath with a fluid sonolucent ultrasound coupling medium which is radio-opaque, and further comprising the step of viewing the inflated sheath fluoroscopically.

* * * * *